US009349272B2

(12) United States Patent  (10) Patent No.: US 9,349,272 B2
Martin et al.  (45) Date of Patent: May 24, 2016

(54) BANDAGE CONTAINER WITH SPEECH, MUSIC, OR INSTRUCTIONAL SOUND EMISSION

(71) Applicant: Medline Industries, Inc., Mundelein, IL (US)

(72) Inventors: Tambra Martin, Trevor, WI (US); Brittany Johnson, Bristol, WI (US)

(73) Assignee: Medline Industries, Inc., Mundelein, IL (US)

( * ) Notice: Subject to any disclaimer, the term of this patent is extended or adjusted under 35 U.S.C. 154(b) by 0 days.

(21) Appl. No.: 14/445,749

(22) Filed: Jul. 29, 2014

(65) Prior Publication Data

US 2016/0035209 A1  Feb. 4, 2016

(51) Int. Cl.
*G08B 21/00* (2006.01)
*G08B 21/18* (2006.01)
*A61F 15/00* (2006.01)

(52) U.S. Cl.
CPC .............. *G08B 21/18* (2013.01); *A61F 15/002* (2013.01)

(58) Field of Classification Search
CPC ....................................................... G08B 21/18
USPC .............. 340/691.1–692, 384.1, 384.6, 384.7
See application file for complete search history.

(56) References Cited

U.S. PATENT DOCUMENTS

| 3,798,806 | A |  | 3/1974 | Sanford |
| 4,102,067 | A |  | 7/1978 | Tarrant |
| 4,193,648 | A | * | 3/1980 | Gargiulo ................... G10F 1/06 108/152 |
| 4,525,393 | A |  | 6/1985 | DiCostanzo |
| 4,702,378 | A |  | 10/1987 | Finkel et al. |
| 4,704,934 | A |  | 11/1987 | Nosrati et al. |
| 4,791,741 | A |  | 12/1988 | Kondo |
| 4,882,966 | A |  | 11/1989 | Silverman |
| 4,973,087 | A |  | 11/1990 | Balogh |
| 5,108,338 | A |  | 4/1992 | Margolis |
| 5,115,472 | A |  | 5/1992 | Park et al. |
| 5,461,187 | A |  | 10/1995 | Dudley |
| 5,850,630 | A |  | 12/1998 | Wilson |
| 6,737,959 | B2 | * | 5/2004 | Ho ....................... B65D 5/4291 340/384.1 |
| 7,203,726 | B2 |  | 4/2007 | Hasegawa |
| 7,658,280 | B2 |  | 2/2010 | Bardet et al. |

(Continued)

FOREIGN PATENT DOCUMENTS

| EP |  | 277276 | 8/1988 |
| EP |  | 394573 | 10/1990 |
| WO | WO 2011139793 |  | 11/2011 |

OTHER PUBLICATIONS

"Notice of Allowance", U.S. Appl. No. 29/497,852, filed Jul. 29, 2014; Mailed May 29, 2015.

(Continued)

*Primary Examiner* — Jeffery Hofsass
(74) *Attorney, Agent, or Firm* — Philip H. Burrus, IV

(57) ABSTRACT

A bandage container (100) is provided with a container body (101) having a base (103) and a plurality of sidewalls (104, 105) extending from the base to define a bandage receiving cavity (201). A lid (102) is coupled to the container body to pivot between a closed position and an open position. One or more bandages (203) are disposed within the bandage receiving cavity. A sensor (901) detects the lid in or transitioning to open position. A sounder (903), operable with the sensor, emits one or more audible sounds (204) when the sensor detects the lid in or transitioning to the radially displaced open position.

20 Claims, 12 Drawing Sheets

(56) References Cited

U.S. PATENT DOCUMENTS

| | | | |
|---|---|---|---|
| 8,159,345 B2 | 4/2012 | Stevens | |
| 2008/0116088 A1 | 5/2008 | Roberts | |
| 2008/0116089 A1 | 5/2008 | Roberts | |
| 2008/0289230 A1 | 11/2008 | Mandelbaum et al. | |
| 2009/0070213 A1 | 3/2009 | Miller et al. | |
| 2009/0165343 A1 | 7/2009 | Miller et al. | |
| 2013/0159445 A1 | 6/2013 | Zonka et al. | |
| 2013/0305574 A1 | 11/2013 | Nelson et al. | |
| 2014/0311936 A1* | 10/2014 | Marks | B65D 25/34 206/457 |

OTHER PUBLICATIONS

"Notice of Allowance", U.S. Appl. No. 29/497,852, filed Jul. 29, 2014; Mailed Oct. 1, 2015.
"Medline Catalog", *ACE Elastic Bandage w/ Hook Closure by 3MHealthcare; Medline Catalog*; http://www.medline.com/catalog/catalog.jsp; Unknown Publication date but believed to be prior to present application filing date.
"Medline Product Catalog", *Adult Eye Patch by Flents; Medline Catalog*; http://www.medline.com/catalog/catalog.jsp; Unknown Publication date but believed to be prior to present application filing date.
"Medline Catalog", *Amerigel Hydrogel Gauze Dressing Packets by Amerx; Medline Catalog*; http://www.medline.com/catalog/catalog.jsp; Unknown Publication date but believed to be prior to present application filing date.
"Medline Catalog", *AmeriGel Hydrogel Gauze Dressings by Amerx; Medline Catalog*; http://www.medline.com/catalog/catalog.jsp; Unknown Publication date but believed to be prior to present application filing date.
"Medline Catalog", *Band-Aid (Multiple Prints) by Johnson & Johnson; Medline Catalog*; http://www.medline.com/catalog/catalog.jsp; Unknown Publication date but believed to be prior to present application filing date.
"Medline Catalog", *Band-Aid by Johnson & Johnson; Medline Catalog*; http://www.medline.com/catalog/catalog.jsp; Unknown Publication date but believed to be prior to present application filing date.
"Medline Catalog", *Band-Aid w/Advanced Healing Blister Cushion by Johnson & Johnson; Medline Catalog*; http://www.medline.com/catalog/catalog.jsp; Unknown Publication date but believed to be prior to present application filing date.
"Medline Catalog", *Bioguard Large Gauze Roll by Derma Science; Medline Catalog*; http://www.medline.com/catalog/catalog.jsp; Unknown Publication date but believed to be prior to present application filing date.
"Medline Catalog", *Circus Stat Strip Bandages by Derma Sciences; Medline Catalog*; http://www.medline.com/catalog/catalog.jsp; Unknown Publication date but believed to be prior to present application filing date.
"Medline Catalog", *Clear Spot Bandages by Johnson & Johnson; Medline Catalog*; http://www.medline.com/catalog/catalog.jsp; Unknown Publication date but believed to be prior to present application filing date.
"Medline Catalog", *Coverlet Eye Occluders by Wilson Ophthalmic Corp; Medline Catalog*; http://www.medline.com/catalog/catalog.jsp; Unknown Publication date but believed to be prior to present application filing date.
"Medline Catalog", *Cuirty O-B Sponges by Covidien; Medline Catalog*; http://www.medline.com/catalog/catalog.jsp; Unknown Publication date but believed to be prior to present application filing date.
"Medline Catalog", *Curad Antibacterial Adhesive Bandages; Medline Catalog*; http://www.medline.com/catalog/catalog.jsp; Unknown Publication date but believed to be prior to present application filing date.
"Medline Catalog", *Curad Athletic Foam Bandages; Medline Catalog*; http://www.medline.com/catalog/catalog.jsp; Unknown Publication date but believed to be prior to present application filing date.
"Medline Catalog", *Curad Butterfly Closure Adhesive Bandages; Medline Catalog*; http://www.medline.com/catalog/catalog.jsp; Unknown Publication date but believed to be prior to present application filing date.
"Medline Catalog", *Curad Clear Adhesive Bandages; Medline Catalog*; http://www.medline.com/catalog/catalog.jsp; Unknown Publication date but believed to be prior to present application filing date.
"Medline Catalog", *Curad Comfort Fabric Bandages; Medline Catalog*; http://www.medline.com/catalog/catalog.jsp; Unknown Publication date but believed to be prior to present application filing date.
"Medline Catalog", *Curad Cotton Bandage Roll; Medline Catalog*; http://www.medline.com/catalog/catalog.jsp; Unknown Publication date but believed to be prior to present application filing date.
"Medline Catalog", *Curad Cupcake Cover Bandages; Medline Catalog*; http://www.medline.com/catalog/catalog.jsp; Unknown Publication date but believed to be prior to present application filing date.
"Medline Catalog", *Curad Dazzle Adhesive Bandage; Medline Catalog*; http://www.medline.com/catalog/catalog.jsp; Unknown Publication date but believed to be prior to present application filing date.
"Medline Catalog", *Curad Extra Stength Waterproof Bandages; Medline Catalog*; http://www.medline.com/catalog/catalog.jsp; Unknown Publication date but believed to be prior to present application filing date.
"Medline Catalog", *Curad Extreme Hold Bandages; Medline Catalog*; http://www.medline.com/catalog/catalog.jsp; Unknown Publication date but believed to be prior to present application filing date.
"Medline Catalog", *Curad Eye Patch; Medline Catalog*; http://www.medline.com/catalog/catalog.jsp; Unknown Publication date but believed to be prior to present application filing date.
"Medline Catalog", *Curad First Aid Kits; Medline Catalog*; http://www.medline.com/catalog/catalog.jsp; Unknown Publication date but believed to be prior to present application filing date.
"Medline Catalog", *Curad Flex-Fabric Bandages; Medline Catalog*; http://www.medline.com/catalog/catalog.jsp; Unknown Publication date but believed to be prior to present application filing date.
"Medline Catalog", *Curad Food Service Adhesive Bandages; Medline Catalog*; http://www.medline.com/catalog/catalog.jsp; Unknown Publication date but believed to be prior to present application filing date.
"Medline Catalog", *Curad Hold Tite Tubular Stretch Bandage; Medline Catalog*; http://www.medline.com/catalog/catalog.jsp; Unknown Publication date but believed to be prior to present application filing date.
"Medline Catalog", *Curad Knee and Elbow Bandages; Medline Catalog*; http://www.medline.com/catalog/catalog.jsp; Unknown Publication date but believed to be prior to present application filing date.
"Medline Catalog", *Curad Mediplast Wart Pads; Medline Catalog*; http://www.medline.com/catalog/catalog.jsp; Unknown Publication date but believed to be prior to present application filing date.
"Medline Catalog", *Curad Performance Series Antibacterial Bandages; Medline Catalog*; http://www.medline.com/catalog/catalog.jsp; Unknown Publication date but believed to be prior to present application filing date.
"Medline Catalog", *Curad Pirates Bandages; Medline Catalog*; http://www.medline.com/catalog/catalog.jsp; Unknown Publication date but believed to be prior to present application filing date.
"Medline Catalog", *Curad Plastic Adhesive Bandages; Medline Catalog*; http://www.medline.com/catalog/catalog.jsp; Unknown Publication date but believed to be prior to present application filing date.
"Medline Catalog", *Curad Pressure Adhesive Bandages; Medline Catalog*; http://www.medline.com/catalog/catalog.jsp; Unknown Publication date but believed to be prior to present application filing date.
"Medline Catalog", *Curad Self Adherent Wrap; Medline Catalog*; http://www.medline.com/catalog/catalog.jsp; Unknown Publication date but believed to be prior to present application filing date.
"Medline Catalog", *Curad Sensitive Skin Bandages; Medline Catalog*; http://www.medline.com/catalog/catalog.jsp; Unknown Publication date but believed to be prior to present application filing date.

(56) References Cited

OTHER PUBLICATIONS

"Medline Catalog", *Curad Silicone Flexible Fabric Bandages; Medline Catalog*; http://www.medline.com/catalog/catalog.jsp; Unknown Publication date but believed to be prior to present application filing date.
"Medline Catalog", *Curad XL Plastic Adhesive Bandages; Medline Catalog*; http://www.medline.com/catalog/catalog.jsp; Unknown Publication date but believed to be prior to present application filing date.
"Medline Catalog", *Dora the Explorer Adhesive Bandages by Johnson & Johnson; Medline Catalog*; http://www.medline.com/catalog/catalog.jsp; Unknown Publication date but believed to be prior to present application filing date.
"Medline Catalog", *Curad Elastic Nets; Medline Catalog*; http://www.medline.com/catalog/catalog.jsp; Unknown Publication date but believed to be prior to present application filing date.
"Medline Catalog", *First Aid Kids by Graham-Field; Medline Catalog*; http://www.medline.com/catalog/catalog.jsp; Unknown Publication date but believed to be prior to present application filing date.
"Medline Catalog", *Fourlex Bandage System; Medline Catalog*; http://www.medline.com/catalog/catalog.jsp; Unknown Publication date but believed to be prior to present application filing date.
"Medline Catalog", *Herbie the Dinosaur Bandages by Derma Sciences; Medline Catalog*; http://www.medline.com/catalog/catalog.jsp; Unknown Publication date but believed to be prior to present application filing date.
"Medline Catalog", *Latex Finger Cot by Tech-Med Services; Medline Catalog*; http://www.medline.com/catalog/catalog.jsp; Unknown Publication date but believed to be prior to present application filing date.
"Medline Catalog", *Looney Tunes Bandages by Derma Sciences; Medline Catalog*; http://www.medline.com/catalog/catalog.jsp; Unknown Publication date but believed to be prior to present application filing date.
"Medline Catalog", *Medigrip Tubular Bandages; Medline Catalog*; http://www.medline.com/catalog/catalog.jsp; Unknown Publication date but believed to be prior to present application filing date.
"Medline Catalog", *Nexcare Comfort Pals Bandages by 3M Healthcare; Medline Catalog*; http://www.medline.com/catalog/catalog.jsp; Unknown Publication date but believed to be prior to present application filing date.
"Medline Catalog", *Non-Sterile Gauze Sponges by Dynarex Corporation; Medline Catalog*; http://www.medline.com/catalog/catalog.jsp; Unknown Publication date but believed to be prior to present application filing date.
"Medline Catalog", *Non-Woven Sponges by Dynarex Corporation; Medline Catalog*; http://www.medline.com/catalog/catalog.jsp; Unknown Publication date but believed to be prior to present application filing date.
"Medline Catalog", *Ortho Glass Wraps by BSN Medical; Medline Catalog*; http://www.medline.com/catalog/catalog.jsp; Unknown Publication date but believed to be prior to present application filing date.
"Medline Catalog", *OrthoFlex Elastic Plaster of Paris Bandages by BSN Medical; Medline Catalog*; http://www.medline.com/catalog/catalog.jsp; Unknown Publication date but believed to be prior to present application filing date.
"Medline Catalog", *Planets & Stars Adhesive Bandages by Derma Sciences; Medline Catalog*; http://www.medline.com/catalog/catalog.jsp; Unknown Publication date but believed to be prior to present application filing date.
"Medline Catalog", *Pre-Cut Tubular Bandages by Medical Action; Medline Catalog*; http://www.medline.com/catalog/catalog.jsp; Unknown Publication date but believed to be prior to present application filing date.
"Medline Catalog", *Reinforced Waterproof Bandges by ASO Corp; Medline Catalog*; http://www.medline.com/catalog/catalog.jsp; Unknown Publication date but believed to be prior to present application filing date.
"Medline Catalog", *Scooby Doo Bandages by Derma Sciences; Medline Catalog*; http://www.medline.com/catalog/catalog.jsp; Unknown Publication date but believed to be prior to present application filing date.
"Medline Catalog", *Spiderman Bandages by Derma Sciences; Medline Catalog*; http://www.medline.com/catalog/catalog.jsp; Unknown Publication date but believed to be prior to present application filing date.
"Medline Catalog", *SpongeBob SquarePants Adhesive Bandages by Jonson & Johnson; Medline Catalog*; http://www.medline.com/catalog/catalog.jsp; Unknown Publication date but believed to be prior to present application filing date.
"Medline Catalog", *Stat Strip Adhesive Bandages; Medline Catalog*; http://www.medline.com/catalog/catalog.jsp; Unknown Publication date but believed to be prior to present application filing date.
"Medline Catalog", *Stat Strip Bandages by Derma Sciences; Medline Catalog*; http://www.medline.com/catalog/catalog.jsp; Unknown Publication date but believed to be prior to present application filing date.
"Medline Catalog", *Sterile Non Woven Post Op Sponges by Dynarex; Medline Catalog*; http://www.medline.com/catalog/catalog.jsp; Unknown Publication date but believed to be prior to present application filing date.
"Medline Catalog", *Stocked First Aid Kit—50 Person by Graham-Field; Medline Catalog*; http://www.medline.com/catalog/catalog.jsp; Unknown Publication date but believed to be prior to present application filing date.
"Medline Catalog", *Tubigrip by Ahmed; Medline Catalog*; http://www.medline.com/catalog/catalog.jsp; Unknown Publication date but believed to be prior to present application filing date.
"Medline Catalog", *Tubigrip Elasticated Tubular Bandages by Molnlyke*; Medline Catalog; http://www.medline.com/catalog/catalog.jsp; Unknown Publication date but believed to be prior to present application filing date.
"Medline Catalog", *Unna-Z Unna Boot Bandages; Medline Catalog*; http://www.medline.com/catalog/catalog.jsp; Unknown Publication date but believed to be prior to present application filing date.
"Medline Catalog", *Vetrap Bandaing Tapes by 3M Healthcare; Medline Catalog*; http://www.medline.com/catalog/catalog.jsp; Unknown Publication date but believed to be prior to present application filing date.
Hofsass, Jeffery "NonFinal OA", U.S. Appl. No. 14/445,768, filed Jul. 29, 2014; Mailed Oct. 1, 2015.
Hofsass, Jeffery "Notice of Allowance", U.S. Appl. No. 14/445,768, filed Jul. 29, 2014; Mailed Jan. 28, 2016.

\* cited by examiner

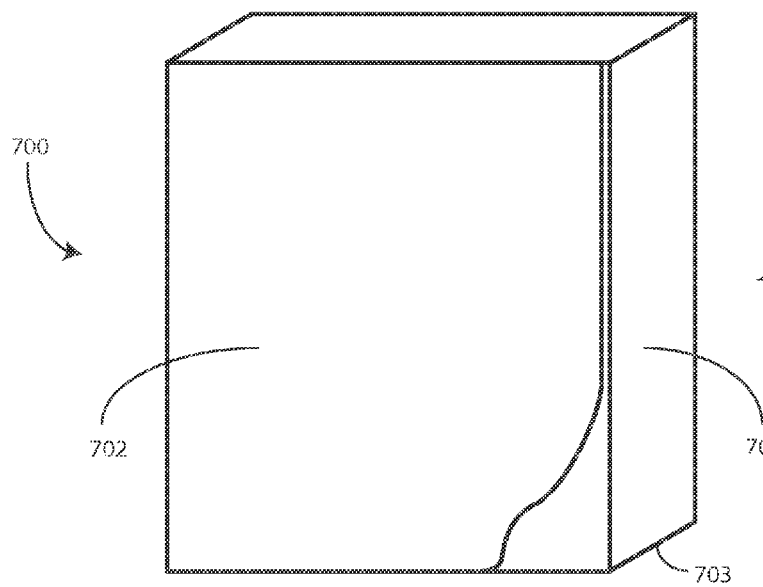
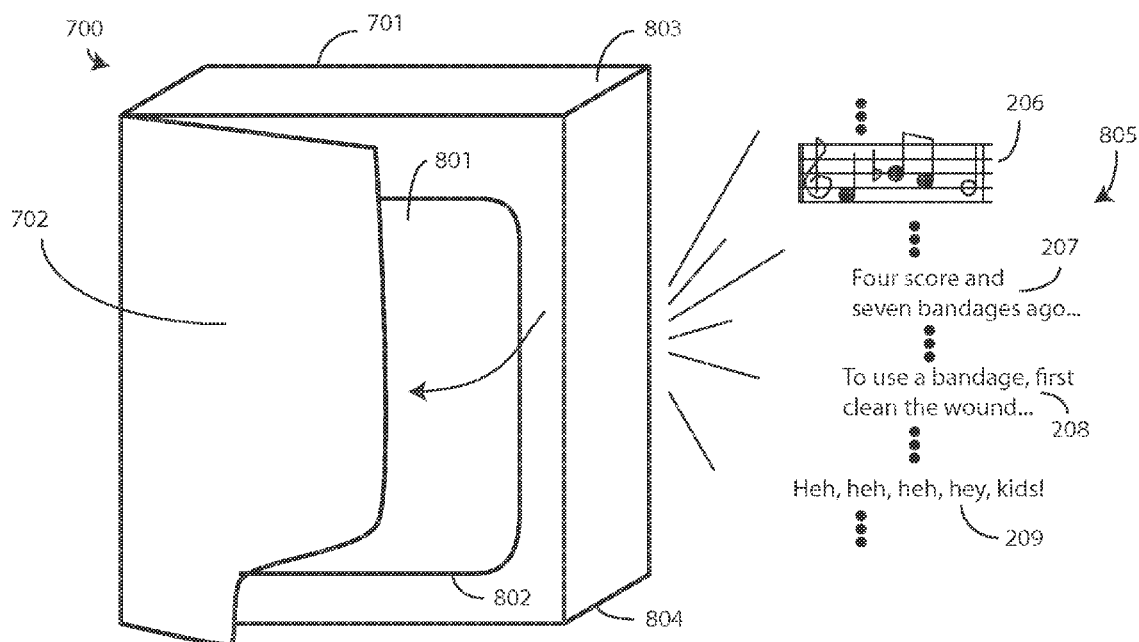

BANDAGE CONTAINER WITH SPEECH, MUSIC, OR INSTRUCTIONAL SOUND EMISSION

BACKGROUND

1. Technical Field

This disclosure relates generally to containers, and more particularly to bandage containers.

2. Background Art

Nicks, cuts, and scrapes are a common childhood hazard. In many cases, when a child injures their skin, the most efficient way to heal the injury is by cleaning the wound, applying an antibiotic or other treatment, and then covering the wound with a bandage. While this process works well to heal the wound, convincing a child to properly apply and wear a bandage can be difficult. Where the child omits wearing a bandage, bacteria or other microbes may enter the wound and cause an infection. It would be advantageous to have something that more readily entices children to properly use and wear bandages.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

FIG. 7 illustrates yet another explanatory bandage container in accordance with one or more embodiments of the disclosure.

FIG. 8 illustrates yet another explanatory bandage container in accordance with one or more embodiments of the disclosure.

Figure 1:
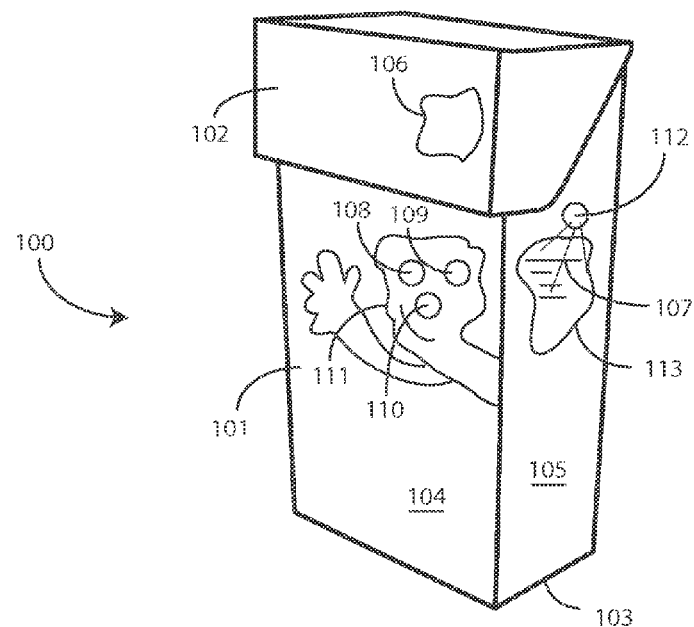
FIG. 1 illustrates one explanatory bandage container in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

It will be appreciated that embodiments of the disclosure described herein may be comprised of one or more conventional processors and unique stored program instructions that control the one or more processors to implement, in conjunction with certain non-processor circuits, some, most, or all of the functions of sound emission from a bandage container as described herein. The non-processor circuits may include, but are not limited to, acoustic drivers, signal amplifiers, signal drivers, clock circuits, power source circuits, and user input devices. As such, these functions may be interpreted as steps of a method to perform sound emission from a bandage container as described below. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used. Thus, methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

As noted above, children are sometimes reluctant to use bandages for wound care. Moreover, even where a particular child is willing to use a bandage, they may not have the knowledge to properly apply and maintain the bandage on the wound. Embodiments of the disclosure provide a bandage container that, when a lid is opened, emits sound. This sound can be entertaining so as to entice a user to more regularly use bandages. Alternatively, the sound can be speech, such as that from a popular character on a television show, or movie. In one embodiment, the emitted sound comprises one or more instructions on how to use the bandages stored within the container. Of course, combinations of music, speech, and instructional material can be used as the emitted sound as well.

Illustrating by example, in one embodiment a bandage container is configured for children. Accordingly, when the lid is opened, music may play to stimulate the child's interest and/or provide comforting sensations to a child that has been injured. While or after this music is playing, a familiar voice, such as that from a popular cartoon or children's show, may deliver speech. For instance, the character might say, "Hello there, Buster! Did you hurt yourself? You look like you could use a bandage." After this, instructional material may be delivered. The character might say, "First, make sure your skin is clean and dry. Then apply the bandage so that the sticky stuff attaches to your skin with the white pad over your boo-boo. And remember, put on a new bandage every day, or more frequently if it gets wet. I want you to feel better soon!" In another embodiment, a bandage container can be configured for adults or people of all ages.

In one embodiment, to make the bandage container more fun to use, while at the same time preserving the sterility of the bandages, the bandage container can include two lids. A first lid encloses a bandage receiving cavity having bandages stowed therein, while a second lid closes to cover the first lid. In one embodiment, the sound emission is triggered when the second lid opens despite the first lid still being closed. Advantageously, this embodiment allows a curious youngster to play with the box and hear fun, interesting, and educational sounds without damaging or contaminating the bandages held within the bandage receiving cavity by the first lid.

Also advantageously, this embodiment allows consumers to "demo" the bandage container in the store to determine whether the particular sounds emitted by the bandage container are suitable for their needs. For example, a manufacturer may offer several different bandage containers, each emitting a different type of sound. One may be particularly well suited for boys, while another is particularly well suited for girls. A boy's mother may prefer a sound stating, "Hey there, did you get hurt playing football?" over one that says, "Does your dolly need a bandage too?" By allowing the mother to test the sound emission without opening the bandage container in the store, she is able to confidently select the most appropriate package of bandages for her child.

In one embodiment where two lids are used, the first lid is sealed to the bandage container with a tamper-proof seal. As noted in the preceding paragraph, in some embodiments a person can try the sound-emission in a store prior to purchase. By sealing the inner lid to the container with a tamper-proof seal, a subsequent purchaser is assured that the bandages disposed within the bandage receiving cavity still have the manufacturer's original integrity.

It should be noted that lids disclosed below can be configured in a variety of ways. For example, in an illustrative embodiment used in most of the figures, a lid covers the end, e.g., the top or the bottom, of the bandage container. However, in other embodiments, such as those shown in FIGS. 7 and 8, the lid can be configured as a door along the front of the bandage container so as to open like a book. Other lid configurations will be obvious to those of ordinary skill in the art having the benefit of this disclosure.

Figure 2:
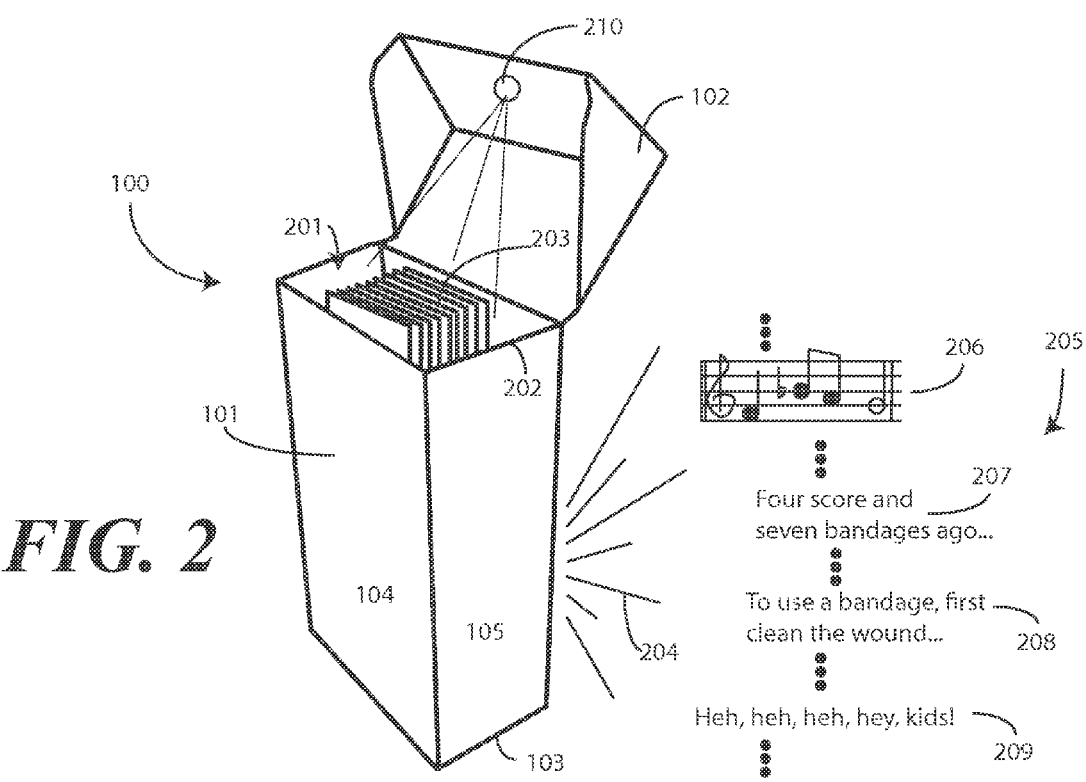
FIG. 2 illustrates one explanatory bandage container in accordance with one or more embodiments of the disclosure.

Turning now to FIGS. 1 and 2, illustrated therein is one embodiment of a bandage container 100 configured in accordance with one or more embodiments of the disclosure. The bandage container 100 of FIG. 1 includes a container body 101 and a lid 102. The container body 101 includes a base 103 and a plurality of sidewalls 104,105. The plurality of sidewalls 104,105 extend distally from the base 103 and define a bandage receiving cavity 201 and an opening 202 of the bandage receiving cavity, each of which is shown in FIG. 2.

The illustrative bandage container 100 of FIG. 1 also includes a lid 102. In this illustrative embodiment, the lid 102 is pivotally coupled to the container body 101. While a pivotally coupled lid will be used herein for illustrative purposes, due to its ease of construction from a die cut (shown in FIG. 17), it should be noted that the lid 102 could take any of a number of other configurations as well. For example, the lid 102 could be removable from the container body 101. The lid 102 could screw, snap, or otherwise attach—and be removable from—the container body 101 in one embodiment. In another embodiment, the lid 102 could be tethered to the container body 101 so as to be separable from, but retained to, the container body 101. Other forms of lid configurations will be obvious to those of ordinary skill in the art having the benefit of this disclosure.

In this illustrative embodiment, the lid 102 is configured to pivot from a closed position covering the opening 202 of the bandage receiving cavity 201, as shown in FIG. 1, and a radially displaced open position shown in FIG. 2. In this illustrative embodiment, pivoting the lid 102 to the radially displaced open position reveals not only the bandage receiving cavity 201 and its opening 202, but the one or more bandages 203 disposed within the bandage receiving cavity 201 as well.

As will be illustrated in more detail below, in this illustrative embodiment the bandage container 100 includes a sensor to detect the lid 102 in—or transitioning to—the radially displaced open position. The sensor is operable with a sounder, which is something capable of producing audible sound 204. When the sensor detects that the lid 102 is in, or alternatively is transitioning to, the radially displaced open position, the sounder can emit the audible sound 204. In one embodiment, this emission of audible sound 204 comprises emitting one or more pre-recorded sounds 205. Examples of the one or more pre-recorded sounds 205 include music 206, speech 207, instructional materials 208, amusing and fanciful utterances 209, or combinations thereof. Accordingly, whenever a user opens the bandage container 100 by pivoting the lid to the radially displaced open position, not only are they able to remove one of the one or more bandages 203 from the container, but they are entertained, enlightened, informed and/or amused in the process.

In one embodiment, the bandage container 100 includes a token 106 indicating that the bandage container 100 is configured for the emission of audible sound 204. As used herein, a "token" takes the principal meaning from the dictionary, which is that of "a think serving as a visible or tangible representation of a fact or quality." Thus, in one embodiment, the token 106 comprises indicia stating, "Open the lid and this box speaks!" In another embodiment, the token 106 is suggestive in nature. As an example, it may ask a rhetorical question that invites a user to manipulate the bandage container 100 as follows: "Ever hear a bandage box talk, buddy?" In another embodiment, the token 106 comprises a fanciful announcement providing an indication of the bandage container's capabilities. For example, the token 106 may state, "Open sesame to hear me talk." These tokens are illustrative only, as others will be obvious to those of ordinary skill in the art having the benefit of this disclosure.

As noted, the audible sound 204 can take a variety of forms. In one embodiment, the audible sound 204 comprises music 206. The music 206 may comprise background music over which speech 207, instructional materials 208, or fanciful utterances 209 are recorded. In another embodiment, the music 206 comprises front music that includes no speech, lyrics, or words. The delivery of music 206 is advantageously effective in at least two ways: First, it entices a user to actually use the bandage container 100 by providing an entertaining experience while the user retrieves a bandage.

Second, the emission of music 206 provides a calming experience that can be especially useful when a person in need of a bandage is injured. This is particularly true when that person is a child. Embodiments of the disclosure contemplate that people in general, and particularly frightened children, find comfort in music and fanciful characters. Music can be used in therapy to help with various issues, such as hyperactivity, temper tantrums, staying quiet and relaxed, and nightmares. Music can also be used in dealing with stress, trauma, or injury. In basic terms, music provides a comforting user experience. For this reason, in one embodiment, when the sensor detects the lid 102 in or transitioning to the radially displaced open position, the sounder is to emit music 206.

In another embodiment, the sounder can be configured to emit speech 207 when the sensor detects the lid 102 in or transitioning to the radially displaced open position. Examples of speech emissions include comforting slogans, poems, soothing narratives, words of encouragement, get well wishes, expressions of sympathy, expressions of empathy, therapeutic statements to reduce pain, and motivational soliloquys. Other types of speech 207 will be obvious to those of ordinary skill in the art having the benefit of this disclosure.

In another embodiment, the sounder can be configured to emit instructional material 208 when the sensor detects the lid 102 in or transitioning to the radially displaced open position. For example, in one embodiment the instructional materials 208 comprises instructions for using one or more of the bandage container 100 or the one or more bandages 203 disposed within the bandage container 100.

In one embodiment the bandage container 100 includes instructional material, warnings, and/or health care suggestions 107 disposed on an exterior of one sidewall 105. Embodiments of the disclosure contemplate that users are sometimes reluctant to take the time to read such instructional material, warnings, and/or health care suggestions 107. Thus, in one embodiment, the instructional materials 208 emitted by the sounder comprises a reading of the instructional material, warnings, and/or health care suggestions 107 to ensure that the instructional material, warnings, and/or health care suggestions 107 are delivered to the user. The instructional materials 208 emitted by the sounder may say, "Apply bandage to clean, dry skin. Change bandage daily or when pad becomes wet," in one embodiment.

In another embodiment, the instructional materials 208 may be supplemental to any instructional material, warnings, or health care suggestions 107 disposed along the bandage container 100. For example, the instructional materials 208 emitted by the sounder may say, "For medical emergencies, please seek professional help." In another embodiment, the instructional materials 208 emitted by the sounder may say, "In case of deep or puncture wounds, or serious burns, consult a physician." In another embodiment, the instructional materials 208 emitted by the sounder may say, "If irritation or redness develops or persists, discontinue use and consult your healthcare provider." Of course, combinations of these can be used. Moreover, other forms of instructional materials 208 suitable for emission by the sounder when the sensor detects the lid 102 in or transitioning to the radially displaced open position will be obvious to those of ordinary skill in the art having the benefit of this disclosure.

In another embodiment, the sounder can be configured to emit fanciful utterances 209 when the sensor detects the lid 102 in or transitioning to the radially displaced open position. Examples of fanciful utterances 209 include catch phrases of famous characters, such as "Elementary, my dear Watson," which is the catch phrase of Sherlock Holmes. Another example of a fanciful utterance 209 would be modifications of tag lines or well-known phrases to make the fanciful utterance 209 more suited for use with the bandage container 100. For example, rather than Santa Claus saying, "Ho ho ho . . . " the fanciful utterance 209 may comprise Santa Claus saying, "Ho ho Noooo!" or "Ho ho oh no!!!" to provide a fanciful utterance 209 that provides a commiserating user experience. Other fanciful utterances 209 will be obvious to those of ordinary skill in the art having the benefit of this disclosure.

In one embodiment, the bandage container 100 optionally includes one or more lights 108,109,110. The one or more lights 108,109,110 can be operable with the sensor to illuminate, flash, or otherwise emit light when the sensor detects that the lid 102 is in—or transitioning to—the radially displaced open position. The inclusion of one or more lights 108,109,110 can provide an even more entertaining, informative, or inviting user experience.

In one embodiment, the one or more lights 108,109,110 form features of a character or fanciful character. For example, in the illustrative embodiment of FIG. 1, the one or more lights 108,109,110 for the eyes and nose of a fanciful character 111 printed on a sidewall 104 of the bandage container 100. The one or more lights 108,109,110 can be used in other ways as well. For instance, in one embodiment the one or more lights 108,109,110 can be configured as fireworks that provide a visual appearance of being launched in the air when the lid 102 is pivoted to the radially displaced open position. Other configurations of one or more lights 108,109, 110 will be obvious to those of ordinary skill in the art having the benefit of this disclosure.

In one embodiment, one or more lights can be used to illuminate to highlight, when actuated by the sensor, one or more of a predefined area of an exterior of the bandage container 100 or a predefined area of an interior of the bandage receiving cavity 201. Illustrating by example, light 112 is used to highlight the instructional material, warnings, and/or health care suggestions 107, which are disposed on a predefined area 113 of the exterior of the bandage container 100. Similarly, light 210 could be used to highlight the interior of the bandage receiving cavity 201, thus making it easier for a user to see the one or more bandages 203 in low-light environments.

In one embodiment, one or more lights can be used to illuminate to highlight, when actuated by the sensor, one or more instructions or illustrations disposed along the bandage container 100 while the sounder emits the one or more prerecorded sounds 205. For example, where the instructional material, warnings, and/or health care suggestions 107 comprise instructions, and the audible sounds 204 comprise instructional materials 208 that reads the instructions, the instructions can be highlighted by light 112 while the instructional materials 208 reads the instructions for using one or more of the bandage container 100 or the one or more bandages 203. Other applications for lights will be obvious to those of ordinary skill in the art having the benefit of this disclosure.

In the illustrative embodiment of FIG. 1, the bandage container 100 is a single-lid container, as the one or more bandages 203 are revealed when the lid 102 is pivoted to the radially displaced, open position. However, it should be noted that embodiments of the disclosure are not so limited. Turning now to FIGS. 3-6, illustrated therein is another embodiment of a bandage container 200 configured in accordance with one or more embodiments of the disclosure.

Figure 3:
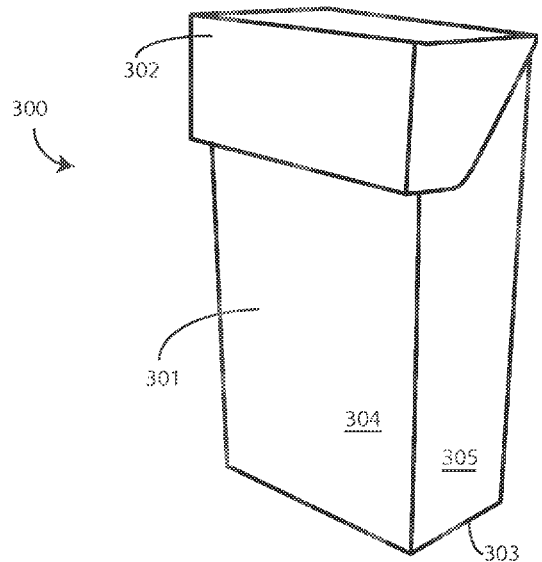
FIG. 3 illustrates another explanatory bandage container in accordance with one or more embodiments of the disclosure.

Beginning with FIG. 3, illustrated therein is a bandage container 300 that looks, at least from the exterior, like the bandage container (100) of FIG. 1. The bandage container 300 of FIG. 3 includes a container body 301 and a lid 302. The container body 301 includes a base 303 and a plurality of sidewalls 304,305. The plurality of sidewalls 304,305 extend distally from the base 303 and define a bandage receiving cavity 501 and an opening 502 of the bandage receiving cavity 501, each of which is shown in FIG. 5.

As with FIG. 1, in this illustrative embodiment, the lid 302 is pivotally coupled to the container body 301. The lid 302 is configured to pivot from a closed position, as shown in FIG. 3, and a radially displaced open position shown in FIG. 4. However, in contrast to the bandage container (100) of FIGS. 1 and 2, the lid 302 does not directly cover the bandage receiving cavity 501 and its opening 502. Instead, the bandage container 300 of FIGS. 3-6 includes another lid 402 that is pivotally coupled to the container body 301. The other lid 402 is shown in FIG. 4.

Figure 4:
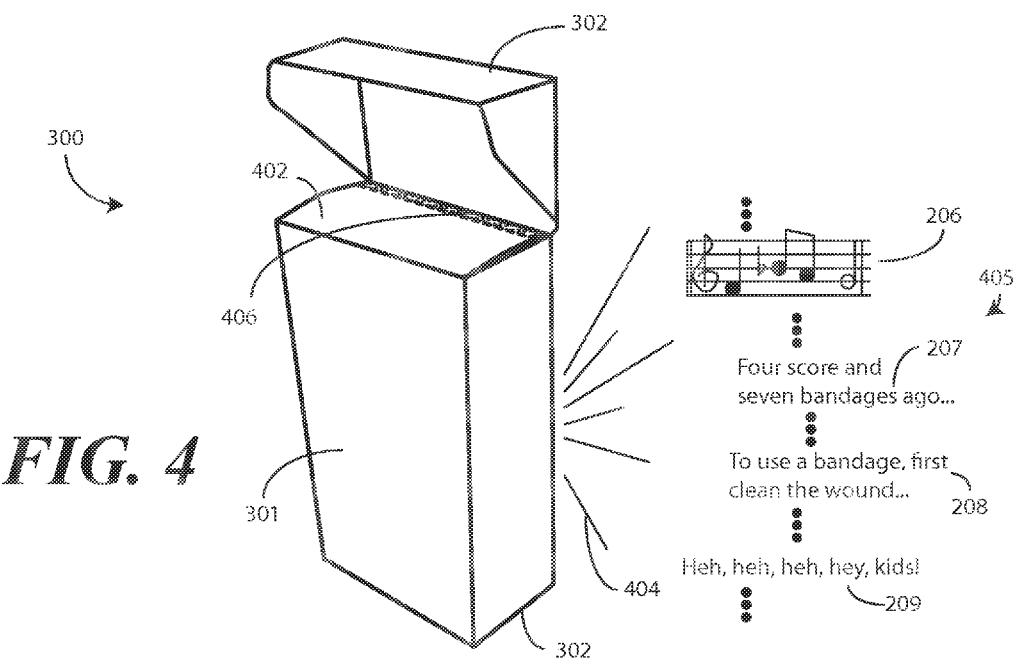
FIG. 4 illustrates another explanatory bandage container in accordance with one or more embodiments of the disclosure.
Figure 5:
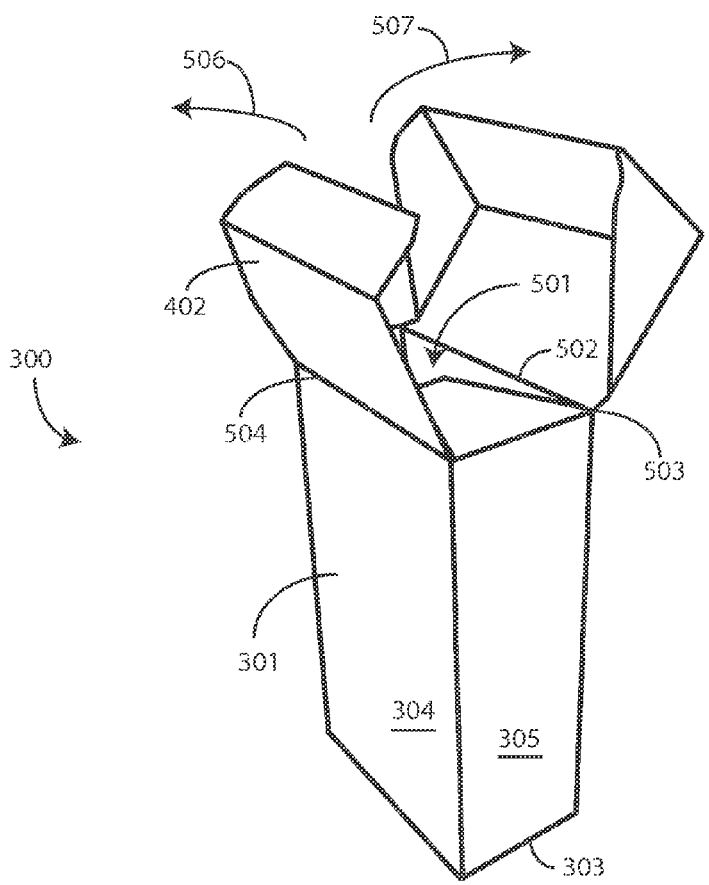
FIG. 5 illustrates another explanatory bandage container in accordance with one or more embodiments of the disclosure.
Figure 6:
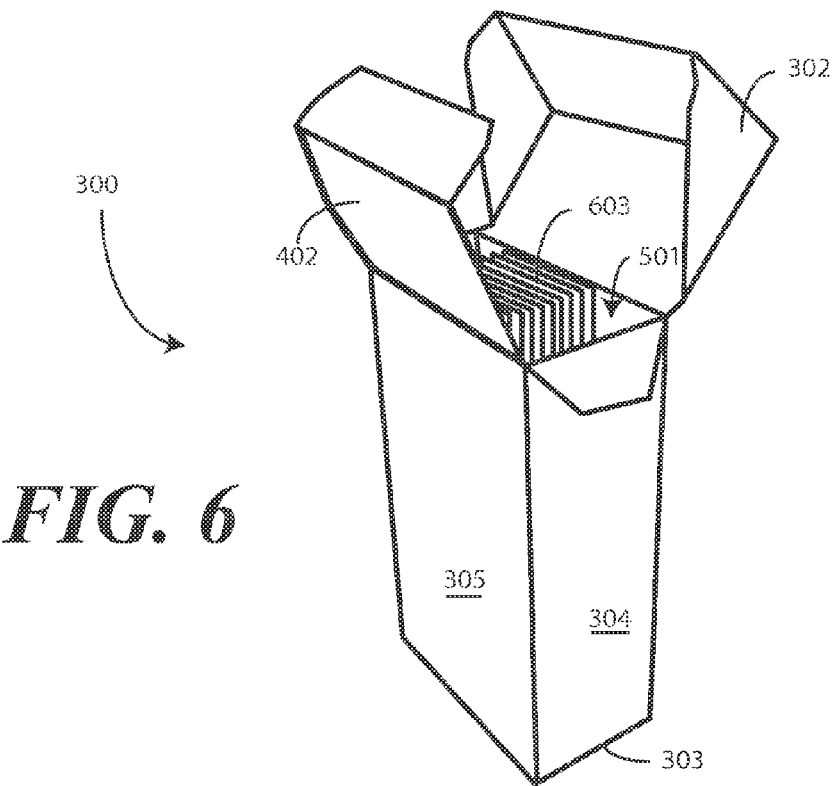
FIG. 6 illustrates another explanatory bandage container in accordance with one or more embodiments of the disclosure.

The other lid 402, like the primary lid 302, is to pivot between another closed position covering the opening 502 of the bandage receiving cavity 501, as shown in FIG. 4, and another radially displaced open position, which is shown in FIG. 5. In this illustrative embodiment, the primary lid 302 is attached to a first side 503 of the container body 301, while the other lid 402 is attached to another side 504 of the container body 301. Thus, as shown in FIG. 5, the lid 302 can pivot radially clockwise 505 relative to the container body 301, while the other lid 402 pivots counterclockwise 506 relative to the container body 301. Had the lid 302 and the other lid 402 been disposed oppositely, the lid 302 would pivot radially counterclockwise 506 relative to the container body 301, while the other lid 402 pivoted clockwise 505 relative to the container body 301. To describe it generally, the lid 302 is to pivot radially one of clockwise 505 or counterclockwise 506 relative to the container body 301, while the other lid 402 pivots radially another of clockwise 505 or counterclockwise 506 relative to the container body 301. In other embodiments, the lid 302 and other lid 402 could be disposed along a common side and could pivot in the same direction as well.

In this embodiment, the other lid 402 serves as a first lid, while the lid 302 serves as a second lid. Thus, the first lid is to selectively transition between a first lid closed position, shown in FIG. 4, where the first lid covers and conceals one or more bandages 603 disposed within the bandage receiving cavity 501, and a first lid radially displaced open position, shown in FIG. 6, where the one or more bandages 603 are revealed. The second lid pivots between a second lid closed position covering the first lid, which is shown in FIG. 3, and a second lid radially displaced open position revealing the first lid, which is shown in FIG. 4.

As with the embodiment of FIGS. 1 and 2, in one embodiment, the bandage container 100 includes a sensor that is operable with a sounder. It should be noted that the sensor can be arranged to detect either the first lid in, or transitioning to, the first lid radially displaced open position, or the second lid in, or transitioning to, the second lid radially displaced open position. With which lid the sensor is operable can be selected by the manufacturer based upon application. However, in the illustrative embodiment of FIGS. 3-6, the sensor is operable to detect the second lid in, or transitioning to, the radially displaced open position as shown in FIG. 4.

While the sensor could be configured to detect the first lid in or transitioning to the first lid open position, configuring the sensor to detect the second lid in or transitioning to the second lid open position offers some advantages. As noted above, in one or more embodiments it is desirable to allow a consumer to try out the bandage container 300 prior to purchase. By allowing the second lid to be manipulated without disturbing the first lid, a user can see how the bandage container 300 works without compromising the sterility of the one or more bandages 603 disposed within the bandage receiving cavity 501. Second, by allowing the second lid to pivot independent of the first lid, a user can play with the bandage container 300 without disturbing the one or more bandages 603.

In one embodiment, the bandage container 300 also includes a sounder operable with the sensor to emit one or more pre-recorded sounds 405 when actuated by the sensor. As with the embodiment of FIGS. 1 and 2, the pre-recorded sounds 405 can be any of music 206, speech 207, instructional materials 208, amusing and fanciful utterances 209, other sounds, or combinations thereof. In this illustrative embodiment, the lid 302 is to close atop the other lid 402. However, the lid 302 is also to pivot to the radially displaced open position to actuate the sounder to emit the one or more pre-recorded sounds 405 while the other lid 402 remains in the closed position. Accordingly, whenever a user pivots the second lid to the radially displaced open position, they are entertained, enlightened, informed and/or amused in the process, all without disturbing the one or more bandages 603 from the container.

In one embodiment, the bandage container 300 also includes a seal 406 to retain the other lid 402 in the closed position until the seal 406 is broken. In one embodiment, the seal 406 is a tamper-proof seal that ensures the one or more bandages 603 disposed within the bandage container 300 remain sterile until the seal 406 is broken. For example, in one embodiment where the bandage container 300 is manufactured from cardboard stock, the seal 406 can be a section of stock with perforations along the other lid 402 and the opening 502 of the bandage receiving cavity 501. A user breaks the seal by pulling the section of stock to tear the two perforations. This frees the other lid 402 to allow it to pivot radially relative to the container body 301. Other types of seals will be obvious to those of ordinary skill in the art having the benefit of this disclosure.

Turning now to FIGS. 7 and 8, illustrated therein is yet another bandage container 700 configured in accordance with one or more embodiments of the disclosure. As with previous embodiments, the bandage container 700 of this illustrative embodiment includes a lid 702 that is pivotally coupled to the container body 701. The lid 702 is configured to pivot from a closed position, as shown in FIG. 7, and a radially displaced open position shown in FIG. 8. However, in contrast to the bandage container (100) of FIGS. 1 and 2, the lid 702 does not pivot along an axis parallel with the base 703. Instead, the lid 702 pivots along an axis perpendicular with the base 703 so as to open like a book.

In this embodiment, when the lid 702 pivots to the radially displaced open position, a window 801 into the bandage container 700 is revealed. In one embodiment the window 801 is manufactured from plastic that spans an aperture 802 along the front major face of the bandage container 700. Thus, by pivoting the lid 702 to the radially displaced open position, a user can see the contents of the bandage container 700 without exposing those contents to the environment. To retrieve the contents, in one embodiment the user opens a second lid disposed at the top 803 or base 703 of the bandage container 700.

As with previous embodiments, the bandage container includes a sensor that is operable with a sounder. The sensor can be arranged to detect the lid 702 in, or transitioning to, an open position. In one embodiment, the bandage container 700 also includes a sounder operable with the sensor to emit one or more pre-recorded sounds 805 when actuated by the sensor. As with the embodiment of FIGS. 1 and 2, the pre-recorded sounds 805 can be any of music 206, speech 207, instructional materials 208, amusing and fanciful utterances 209, other sounds, or combinations thereof. Accordingly, whenever a user pivots the second lid to the radially displaced open position, they are entertained, enlightened, informed and/or amused in the process, all without disturbing the contents of the container.

Figure 9:
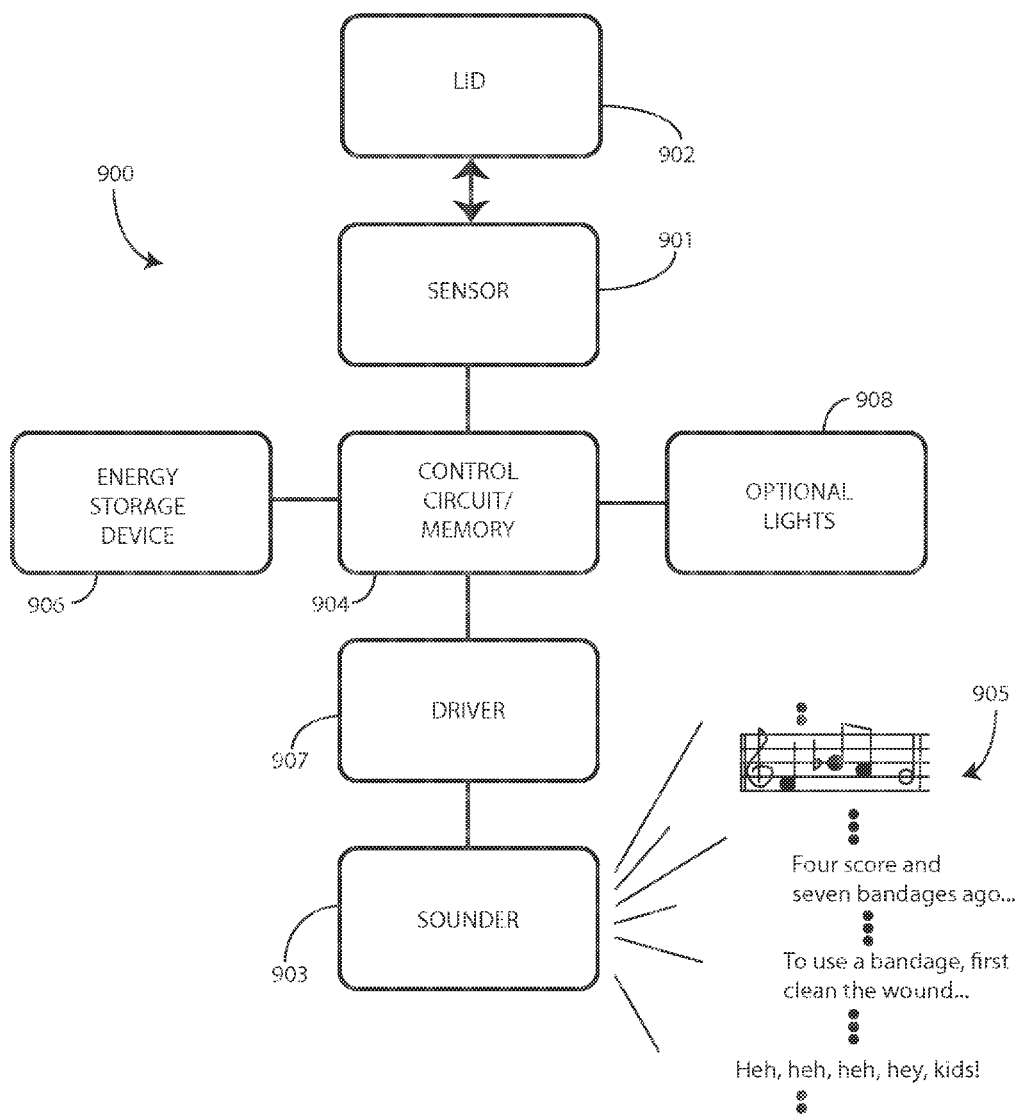
FIG. 9 illustrates a schematic block diagram of a bandage container in accordance with one or more embodiments of the disclosure.

Turning now to FIG. 9, illustrated therein is one explanatory schematic block diagram of a sounding mechanism 900 configured in accordance with one or more embodiments of the disclosure. The illustrative sounding mechanism 900 of FIG. 9 includes a sensor 901 that is operable to detect a lid 902 in or transitioning to an open position relative to a bandage container. A sounder 903, operable with the sensor 901, is to emit one or more pre-recorded audio sounds 905 when the sensor 901 detects the lid 902 in or transitioning to an open position as previously described. Examples of sounders include loudspeakers, piezoelectric transducers, and other acoustic transducers.

In one embodiment, one or more control circuits 904 serve as the operational hub of the sounding mechanism 900. The one or more control circuits 904 also serve as an interface between the sensor 901 and the sounder 903. The one or more control circuits 904 can include a processing circuit such as a microprocessor or programmable logic, and can be configured to be operable with the sensor 901. For instance, one or more control circuits 904, through embedded executable code or programmed logic, can be configured to actuate the sounder 903 in response to electrical signals received from the sensor 901. In one embodiment, the one or more control circuits 904 include on-board memory, or are operable with separate memory devices, which store data corresponding to recorded sound expressions. For example, the memory devices can store the pre-recorded audio sounds 905.

Where one or more control circuits 904 are used, additional features can be added as well. For example, the one or more control circuits 904 can be configured to emit the pre-recorded audio sounds 905 only for a predetermined duration or time period. The one or more control circuits 904 can also cycle through different pre-recorded audio sounds 905, in series or randomly, to provide the user with a more dynamic user experience.

An energy storage device 906, such as a lithium-ion battery, can be included to provide power to the various components. In one or more embodiments, one or more drivers 907, operable with the sounder, can amplify the pre-recorded audio sounds 905 and can deliver one or more of the recorded sound expressions to the sounder 903. As noted above with reference to FIGS. 1 and 2, one or more lights can be optionally included.

Figure 10:
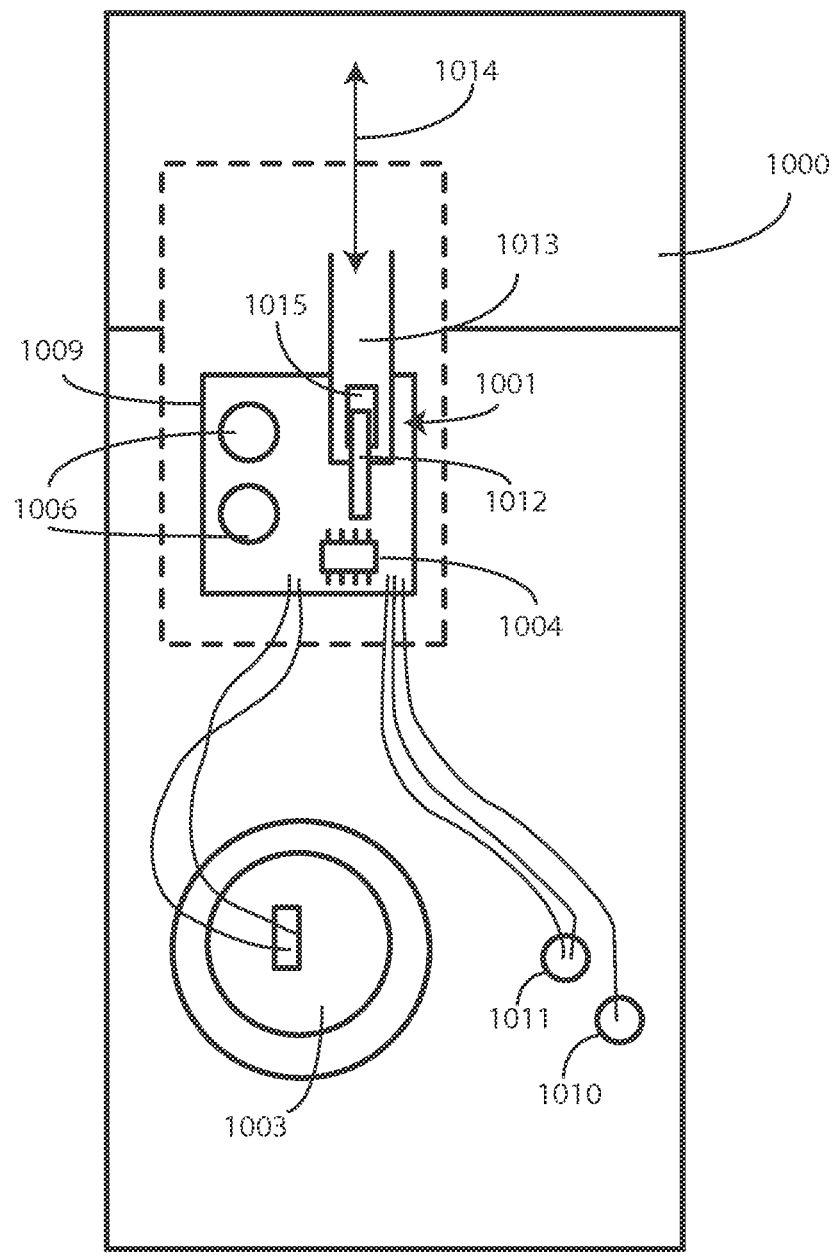
FIG. 10 illustrates one explanatory component carrier in accordance with one or more embodiments of the disclosure.

Turning now to FIG. 10, illustrated therein are physical components corresponding to the schematic block diagram components of FIG. 9. In FIG. 10, the various components have been disposed along a carrier 1000, which can be a plastic or film layer, or alternatively a section of material that is common with the bandage container into which the components will be placed, e.g., cardboard stock.

In the illustrative embodiment of FIG. 10, a control circuit 1004 is disposed on a circuit board 1009, which may be a flexible printed circuit board, rigid printed circuit board, or other. The control circuit 1004 includes an on-board memory device and on board drivers for the sounder 1003, which in this embodiment is a cone-driven loudspeaker. Two coin size batteries 1006 serve as energy storage devices for the control circuit 1004 and the sensor 1001. Two lights 1010,1011 are operable with the control circuit 1004 in this embodiment as well.

In this embodiment, the sensor 1001 comprises a spring contact switch 1012 and an insulating slider 1013. As will be shown below in FIG. 11, the insulating slider 1013 can be coupled to the lid of a bandage container. When the lid is opened, the insulating slider 1013 translates 1014. This allows the spring contact switch 1012 to close by contacting a conductive pad 1015. This actuates the sounder 1003 by delivering electrical signals to the control circuit 1004. The control circuit 1014 can then actuate the sounder 1003 and optionally the one or more lights 1010,1011.

Figure 11:
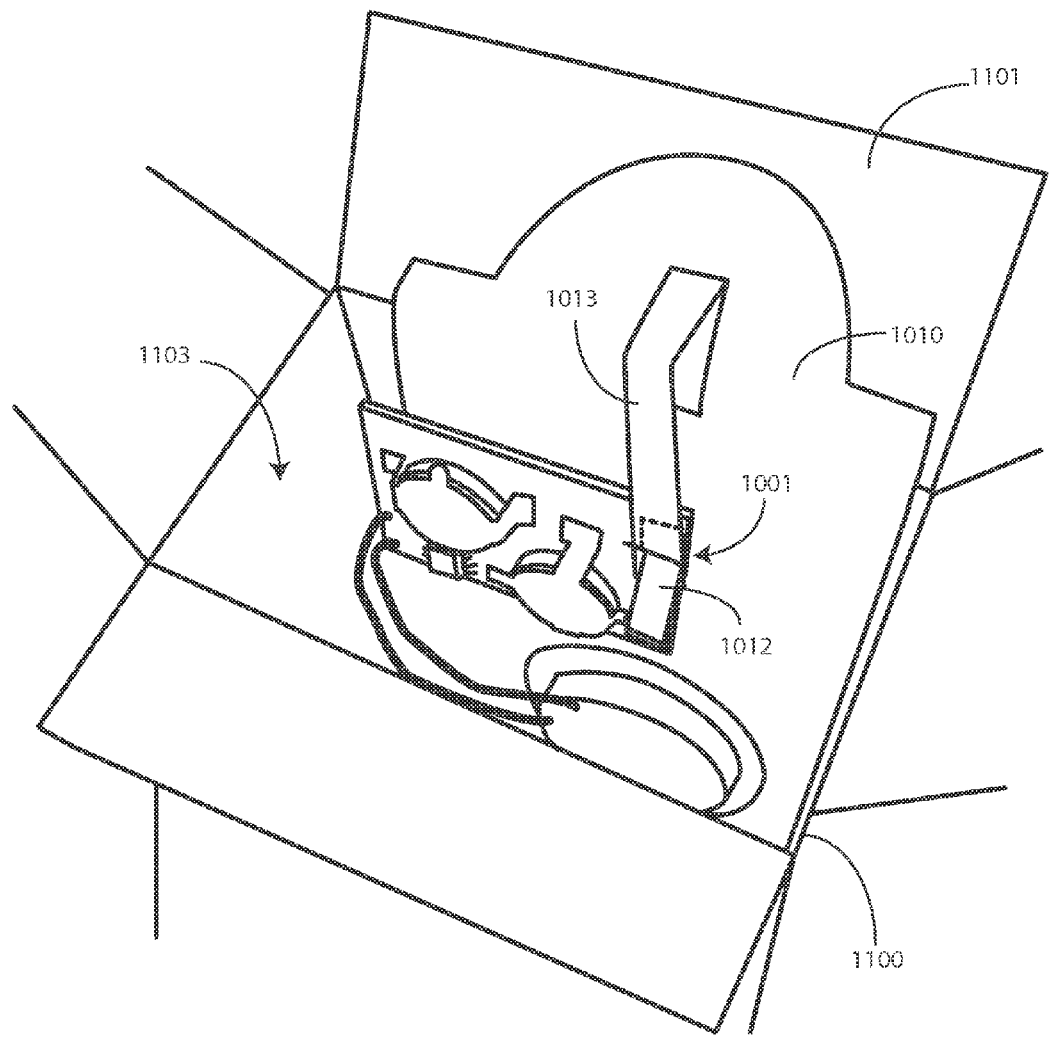
FIG. 11 illustrates one explanatory component carrier arranged in a bandage container in accordance with one or more embodiments of the disclosure.

Turning now to FIG. 11, the carrier 1000 has been disposed in a bandage container 1100. The lid 1101 of the bandage container 1100 has been coupled to the insulating slider 1013 such that when the lid 1101 pivots from a closed position to a radially displaced open position, the insulating slider 1013 translates to close the spring contact switch 1012 to actuate the sensor 1001 as previously described.

Figure 12:
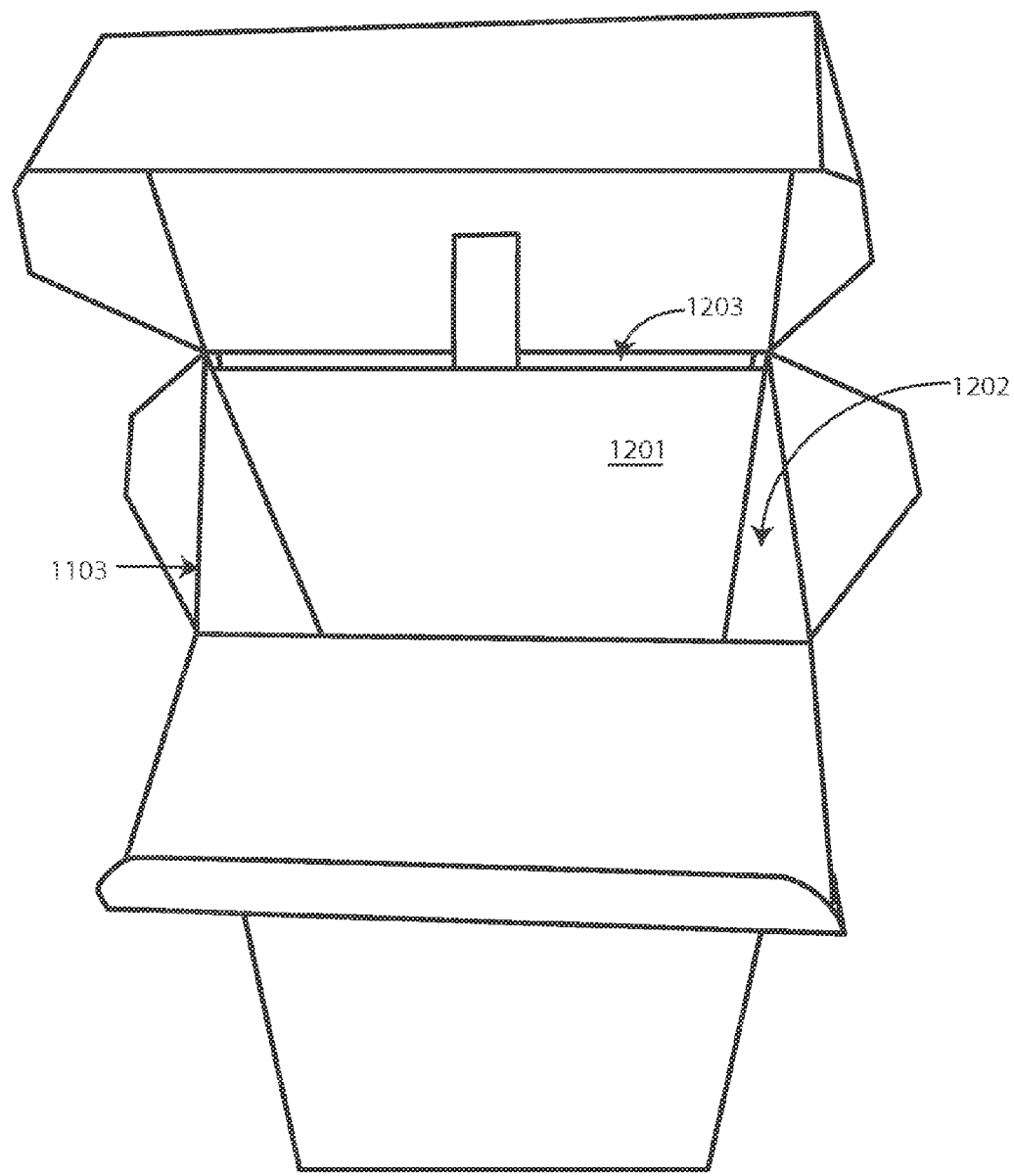
FIG. 12 illustrates one explanatory component carrier arranged in another bandage container in accordance with one or more embodiments of the disclosure.

Embodiments of the disclosure contemplate that it may be advantageous to conceal the carrier 1000 and its various components within the bandage container 1100. In one embodiment, this is accomplished by including a partition to divide the bandage receiving cavity 1103 into separate compartments. Turning briefly to FIG. 12, illustrated therein is such a partition 1201. The partition 1201 divides the bandage receiving cavity 1103 into a first portion 1202 and a second portion 1203. The one or more bandages can disposed within the first portion 1202, while the sounder (1003) is disposed within the second portion 1203.

Figure 13:
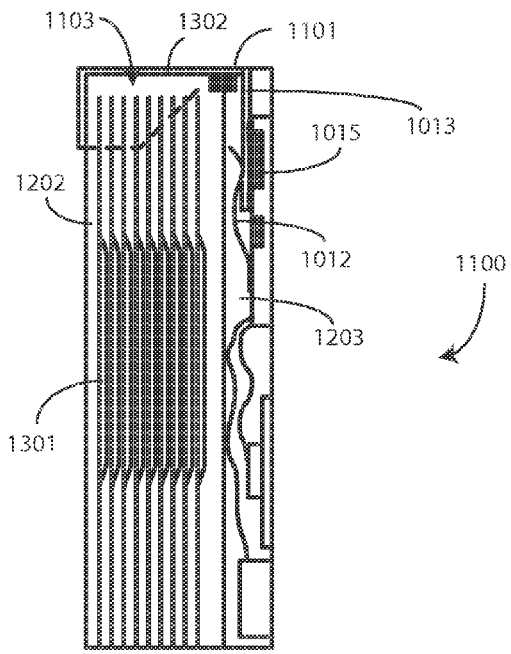
FIG. 13 illustrates a sectional view of one explanatory bandage container in accordance with one or more embodiments of the disclosure.
Figure 14:
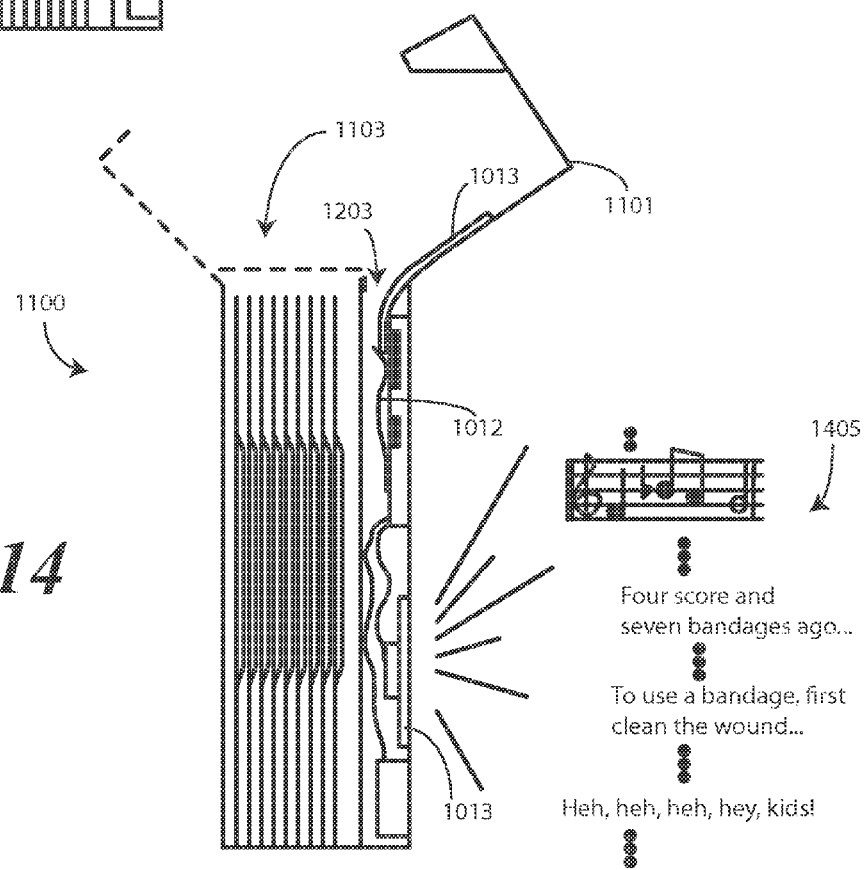
FIG. 14 illustrates another sectional view of one explanatory bandage container in accordance with one or more embodiments of the disclosure.

Operation of this embodiment is shown in FIGS. 13 and 14. Turning now to these figures, at FIG. 13 the bandage container 1100 is shown with its lid 1101 in the closed position. Accordingly, the insulating slider 1013 has translated downward into the second portion 1203 of the bandage receiving cavity 1103. This separates the spring contact switch 1012 from the conductive pad 1015. One or more bandages 1301 are disposed in the first portion 1202 of the bandage receiving cavity 1103, which is sealed with a second lid 1302 in this illustrative embodiment.

At FIG. 14, a user has pivoted the lid 1101 to a radially displaced open position. This causes the insulating slider 1013 to translate upward and out of the second portion 1203 of the bandage receiving cavity 1103. This causes the spring contact switch 1012 to close the spring contact switch 1012 to actuate the sensor as previously described. The sounder 1003 can then emit one or more pre-recorded sounds when the sensor detects the lid 1101 in or transitioning to the radially displaced open position.

Figure 15:
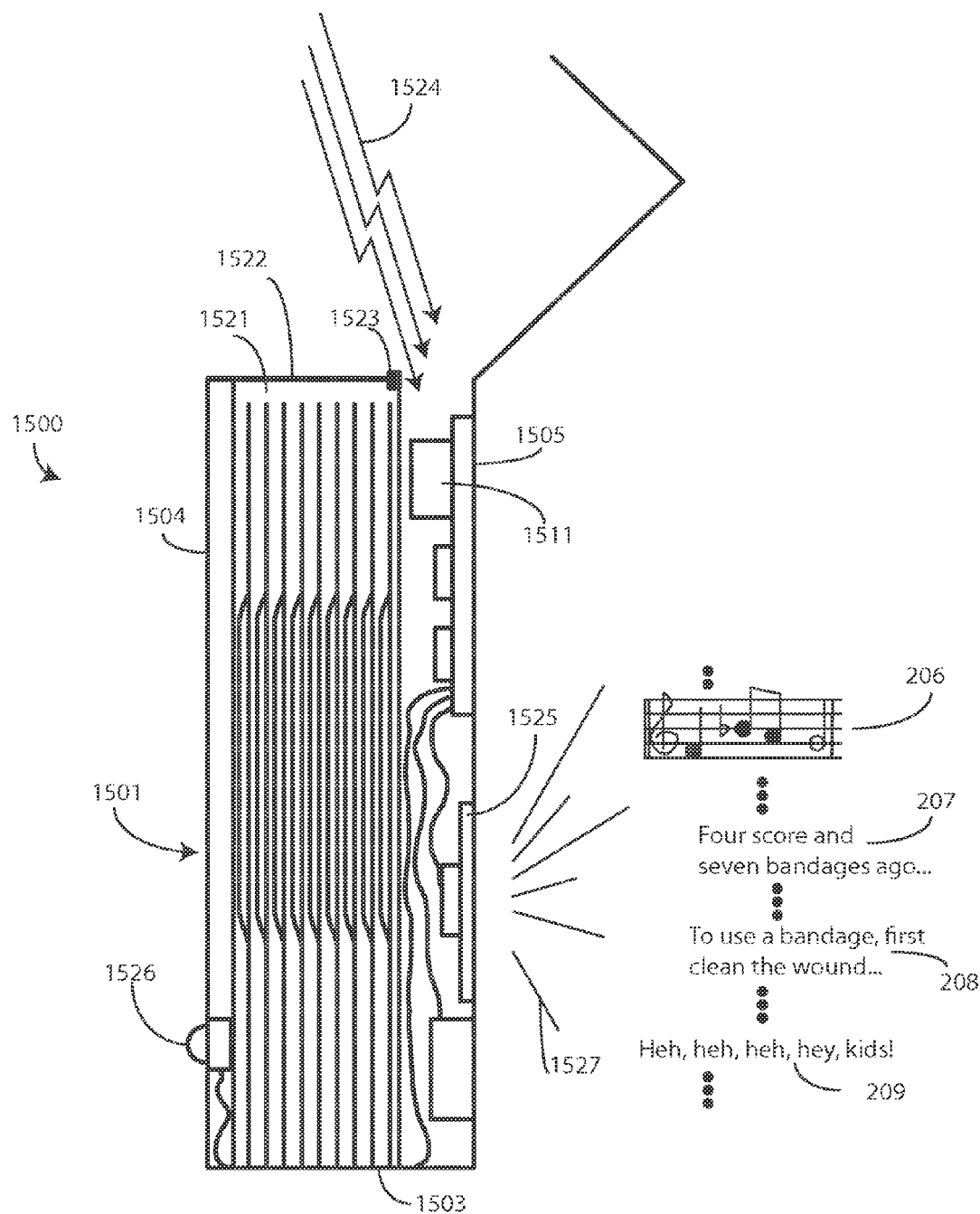
FIG. 15 illustrates a sectional view of another explanatory bandage container in accordance with one or more embodiments of the disclosure.

A spring contact switch 1012 is but one configuration of a sensor suitable for use with one or more embodiments of the disclosure. In other embodiments, a light sensor can be used as the sensor. Turning now to FIG. 15, illustrated therein is such an embodiment.

In FIG. 15, the sensor 1511 is a light detector. As with previous embodiments, the bandage container 1500 includes a container body 1501 and a lid 1502. The container body 1501 includes a base 1503 and a plurality of sidewalls 1504, 1505. The plurality of sidewalls 1504,1505 extends distally from the base 1503 and defines a bandage receiving cavity 1521. In this embodiment, the bandage receiving cavity 1521 is sealed by a second lid 1522 and a tamper-proof seal 1523.

The lid 1502 is pivotally coupled to the container body 1501. In this illustrative embodiment, the lid 1501 is configured to pivot from a closed position covering the second lid 1522, and a radially displaced open position shown in FIG. 15.

The sensor 1511 detects the lid 1501 in—or transitioning to—the radially displaced open position by detecting light. The sensor 1511 is operable with a sounder 1525, and optionally one or more lights 1526. When the lid 1501 is in, or alternatively is transitioning to, the radially displaced open position, the sensor 1511 receives light 1524 to detect this lid state. The sounder 1525, operable with the sensor 1511, can emit the audible sound 1527. In one embodiment, this emission of audible sound 1527 comprises emitting one or more of music 206, speech 207, instructional materials 208, amusing and fanciful utterances 209, or combinations thereof.

Figure 16:
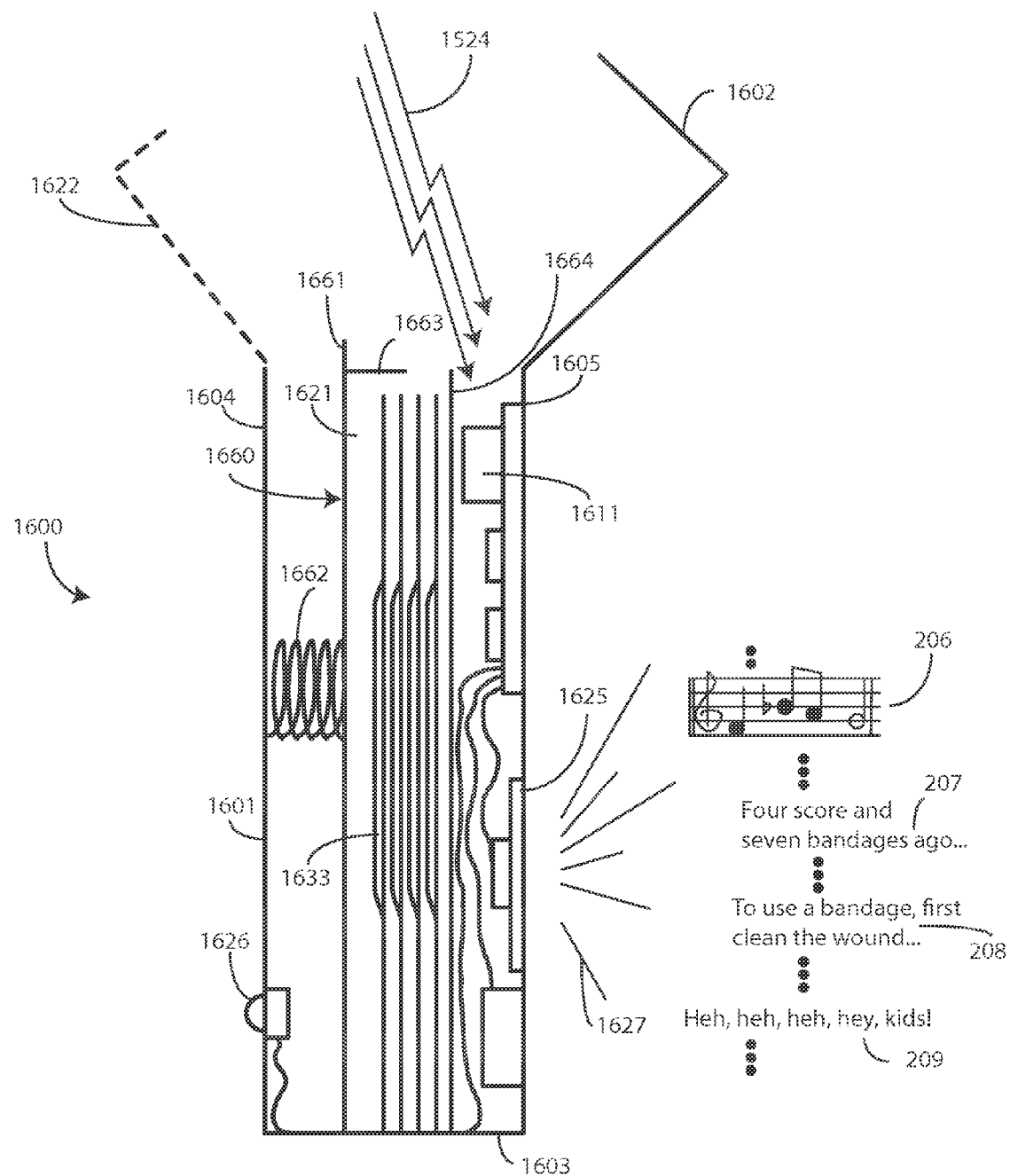
FIG. 16 illustrates a sectional view of yet another explanatory bandage container in accordance with one or more embodiments of the disclosure.

Turning now to FIG. 16, illustrated therein is an alternative bandage container 1600 configured in accordance with one or more embodiments of the disclosure. As with previous embodiments, the bandage container 1600 includes a container body 1601 and a lid 1602. The container body 1601 includes a base 1603 and a plurality of sidewalls 1604,1605. The plurality of sidewalls 1604,1605 extends distally from the base 1603 and defines a bandage receiving cavity 1621. While the bandage container 1600 can optionally include a second lid 1522, the embodiment of FIG. 16 employs a different mechanism for retaining the one or more bandages 1633 within the bandage receiving cavity 1621.

In this illustrative embodiment, the one or more bandages 1633 are retained within the bandage receiving cavity 1621 by an ell 1660. The ell 1660 includes a finger tab 1661 and is to translate from a first position to a second position in response to user actuation. When the ell 1660 is in a default position, a spring 1662 biases the ell to a closed position in which a lid member 1663 of the ell 1660 engages the partition 1664 to retain the one or more bandages 1633 in the bandage receiving cavity 1621. A user can actuate the finger tab 1661 to compress the spring 1662 and pull back the ell 1660, thereby revealing the one or more bandages 1633. Thus, the one or more bandages 1633 are enclosed between the ell 1660 and the partition 1664 when the ell is in the first, closed position. The spring 1662 biases the ell 1660 in the first, closed position in this embodiment. The one or more bandages 1633 are exposed in response to user actuation when the ell 1660 is moved to the second position by compression of the spring 1662.

As with the embodiment of FIG. 15, the sensor 1611 is a light detector. The lid 1602 is pivotally coupled to the container body 1601. In this illustrative embodiment, the lid 1602 is configured to pivot from a closed position covering the ell 1660, and optionally the second lid 1622 where included, and the radially displaced open position shown in FIG. 15.

The sensor 1611 detects the lid 1602 in—or transitioning to—the radially displaced open position by detecting light 1524. The sensor 1611 is operable with a sounder 1625, and optionally one or more lights 1626. When the lid 1602 is in, or alternatively is transitioning to, the radially displaced open position, the sensor 1611 receives light 1524 to detect this lid state. The sounder 1625, operable with the sensor 1611, can emit the audible sound 1627. In one embodiment, this emission of audible sound 1627 comprises emitting one or more of music 206, speech 207, instructional materials 208, amusing and fanciful utterances 209, or combinations thereof.

Figure 17:
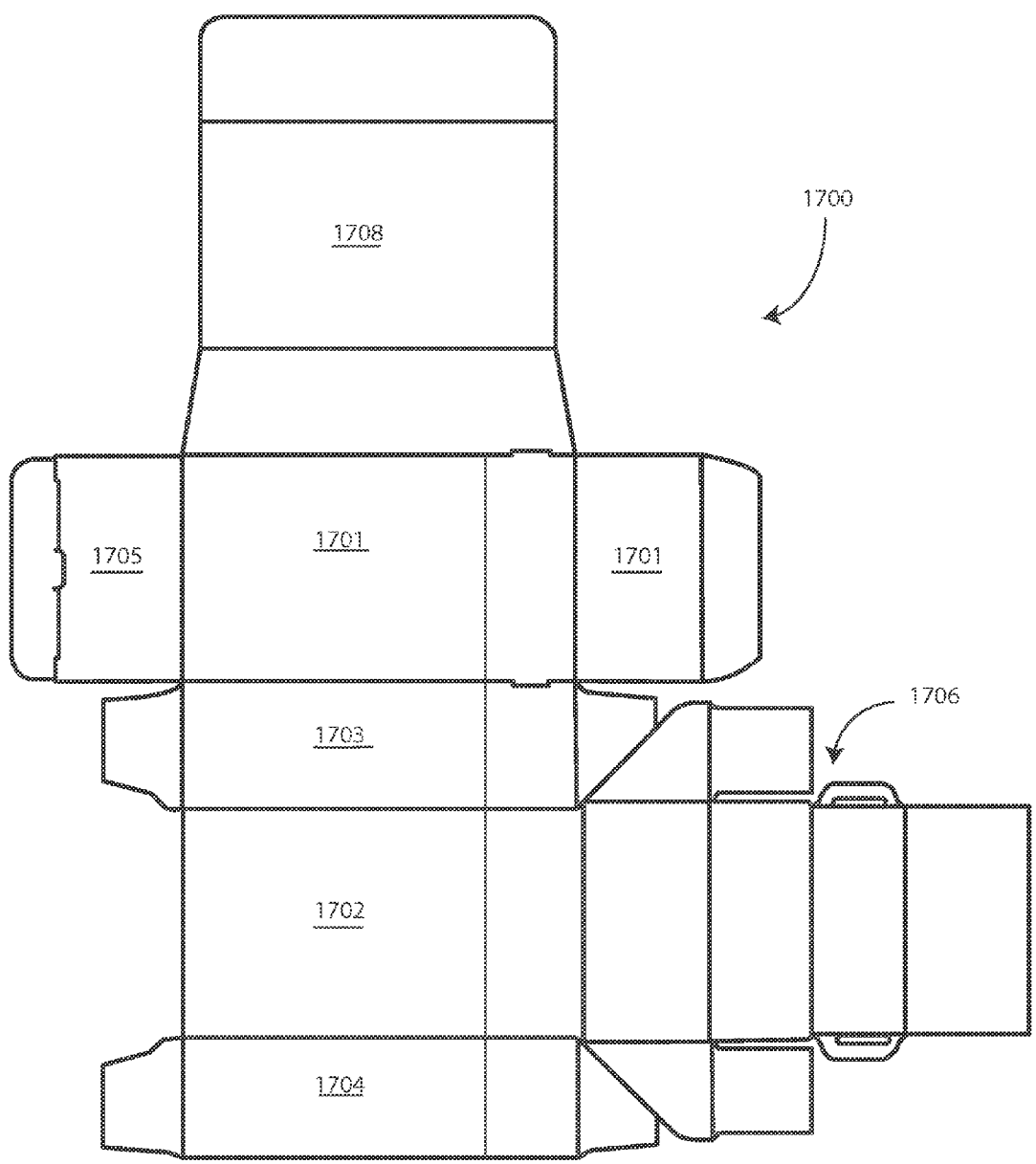
FIG. 17 illustrates an explanatory die cut for one explanatory bandage container in accordance with one or more embodiments of the disclosure.

Turning now to FIG. 17, illustrated therein is a die cut 1700 suitable for making bandage containers configured in accordance with multiple embodiments described above. Shown in FIG. 17 are a front major sidewall 1701, a rear major sidewall 1702, and two minor sidewalls 1703,1704. The sidewalls 1701,1702,1703,1704 extend distally from a base 1705. In this embodiment, the front major sidewall 1701 terminates at a first lid 1706, while the rear major sidewall 1702 terminates at a second lid 1707. A partition 1708 is provided for concealing carriers, sounders, circuit boards, and other components as previously described with reference to FIG. 12. The die cut 1700 of FIG. 17 makes fabrication of bandage containers suitable for use with various embodiments of the disclosure simple and cost-effective.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A bandage container, comprising:
   a container body comprising a base and a plurality of sidewalls extending from the base to define a bandage receiving cavity, the plurality of sidewalls defining an opening of the bandage receiving cavity;
   a lid pivotally coupled to the container body, the lid to pivot between a closed position covering the opening and a radially displaced open position;
   another lid pivotally coupled to the container body, the another lid to pivot between another closed position covering the opening and another radially displaced open position;
   one or more bandages disposed within the bandage receiving cavity;
   a sensor to detect the lid in or transitioning to the radially displaced open position; and
   a sounder, operable with the sensor, the sounder to emit one or more pre-recorded sounds when the sensor detects the lid in or transitioning to the radially displaced open position.

2. The bandage container of claim 1, the sensor comprising:
   a spring contact switch; and
   an insulating slider;
   the insulating slider coupled to the lid;
   the insulating slider to translate when the lid pivots to the radially displaced open position;
   the spring contact switch to close when the insulating slider translates to actuate the sensor.

3. The bandage container of claim 1, the sensor comprising a light detector, the lid to pivot from the closed position to the radially displaced open position to expose the light detector to light to actuate the light detector.

4. The bandage container of claim 1, further comprising a partition dividing the bandage receiving cavity into a first portion and a second portion, the one or more bandages disposed within the first portion, the sounder disposed within the second portion.

5. The bandage container of claim 1, the lid attached to a first side of the container body to pivot radially one of clockwise or counterclockwise relative to the container body, the another lid to pivot radially another of clockwise or counterclockwise relative to the container body.

6. The bandage container of claim 5, the lid to close atop the another lid, the lid to pivot to the radially displaced open position to actuate the sounder to emit the one or more pre-recorded sounds while the another lid remains in the another closed position.

7. The bandage container of claim 6, further comprising a seal to retain the another lid in the another closed position until the seal is broken.

8. The bandage container of claim 6, the one or more pre-recorded sounds one or more of music or speech.

9. The bandage container of claim 6, the one or more pre-recorded sounds comprising instructions for using one or more of the bandage container or the one or more bandages.

10. The bandage container of claim 6, further comprising one or more lights, operable with the sensor, to illuminate when the sensor detects the lid in or transitioning to the radially displaced open position.

11. The bandage container of claim 10, the one or more lights to flash when the sensor detects the lid in or transitioning to the radially displaced open position.

12. The bandage container of claim 4, further comprising an ell to translate from a first position to a second position, the one or more bandages enclosed between the ell and the partition when the ell is in the first position, the one or more bandages exposed when the ell is in the second position.

13. The bandage container of claim 12, further comprising a spring to bias the ell in the first position.

14. The bandage container of claim 4, the sounder comprising:
  a memory device to store data corresponding to recorded sound expressions;
  a loudspeaker;
  one or more drivers, operable with the loudspeaker and the memory device, to deliver one or more of the recorded sound expressions to the loudspeaker; and
  an energy storage device.

15. A bandage container, comprising:
  a container body comprising a base and a plurality of sidewalls extending from the base to define a bandage receiving cavity, the plurality of sidewalls defining an opening of the bandage receiving cavity;
  one or more bandages disposed within the bandage receiving cavity;
  a first lid, the first lid to selectively transition between a first lid closed position concealing the one or more bandages and a first lid open position revealing the one or more bandages;
  a second lid pivotally coupled to the container body, the second lid to pivot between a second lid closed position covering the first lid and a second lid radially displaced open position revealing the first lid;
  a sensor to detect one of the first lid in or transitioning to the first lid open position or the second lid in or transitioning to the second lid radially displaced open position; and
  a sounder, operable with the sensor, the sounder to emit one or more pre-recorded sounds when actuated by the sensor.

16. The bandage container of claim 15, the sensor to detect the first lid in or transitioning to the first lid open position.

17. The bandage container of claim 15, the first lid pivotally coupled to the container body, the first lid and the second lid to pivot in opposite directions.

18. The bandage container of claim 15, the first lid comprising an ell, the ell spring-biased to the first lid closed position.

19. The bandage container of claim 15, further comprising one or more lights, operable with the sensor, the one or more lights to illuminate to highlight, when actuated by the sensor, one or more of a predefined area of an exterior of the bandage container or a predefine area of an interior of the bandage receiving cavity.

20. The bandage container of claim 15, further comprising one or more lights, operable with the sensor, the one or more lights to illuminate to highlight, when actuated by the sensor, one or more instructions or illustrations disposed along the bandage container while the sounder emits the one or more pre-recorded sounds, the one or more pre-recorded sounds comprising instructions for using one or more of the bandage container or the one or more bandages.

* * * * *